US012594120B2

(12) United States Patent
Zhang et al.

(10) Patent No.: US 12,594,120 B2
(45) Date of Patent: Apr. 7, 2026

(54) WATER-COOLED FLEXIBLE MICROWAVE ABLATION PROBE

(71) Applicant: COSWAVE MEDICAL INC., Richmond (CA)

(72) Inventors: Peng Zhang, Vancouver (CA); Ting Yang, Richmond (CA); Yixin Yang, Burnaby (CA)

(73) Assignee: COSWAVE MEDICAL INC., Richmond (CA)

( * ) Notice: Subject to any disclaimer, the term of this patent is extended or adjusted under 35 U.S.C. 154(b) by 252 days.

(21) Appl. No.: 18/599,959

(22) Filed: Mar. 8, 2024

(65) Prior Publication Data

US 2025/0281235 A1 Sep. 11, 2025

(51) Int. Cl.
*A61B 18/18* (2006.01)
*A61B 18/00* (2006.01)

(52) U.S. Cl.
CPC ..................... *A61B 18/1815* (2013.01); *A61B 2018/00023* (2013.01); *A61B 2018/00035* (2013.01); *A61B 2018/00083* (2013.01); *A61B 2018/00178* (2013.01); *A61B 2018/00577* (2013.01); *A61B 2018/1823* (2013.01); *A61B 2018/1838* (2013.01); *A61B 2018/1853* (2013.01)

(58) Field of Classification Search
CPC ...... A61B 18/1815; A61B 2018/00023; A61B 2018/00035; A61B 2018/00083; A61B 2018/00178; A61B 2018/00577; A61B 2018/1823; A61B 2018/1838; A61B 2018/1846; A61B 2018/1853; A61B 2018/1861; A61B 2018/1892
See application file for complete search history.

(56) References Cited

U.S. PATENT DOCUMENTS

| | | | |
|---|---|---|---|
| 8,965,536 B2* | 2/2015 | Bonn ..................... | A61B 18/18 607/156 |
| 2012/0310228 A1* | 12/2012 | Bonn ................. | A61B 18/1815 606/33 |
| 2016/0051327 A1* | 2/2016 | Brannan ................ | A61B 34/20 606/33 |
| 2017/0265940 A1* | 9/2017 | Prakash ............. | A61B 18/1815 |
| 2019/0069951 A1* | 3/2019 | Hancock ............ | A61B 18/1492 |
| 2021/0220048 A1* | 7/2021 | Zhang ................ | A61B 18/1815 |

* cited by examiner

*Primary Examiner* — Khadijeh A Vahdat

(57) ABSTRACT

Examples of a water-cooled microwave ablation probe are disclosed. The probe comprises a feed cable and an antenna with a radiator, a reflector and a dielectric material therein between. An outer sheath with a flexible tubular body encases the feed cable and portion of the antenna. A front-end of the outer sheath is connected to the antenna such that the radiating head extends out of the outer sheath. The outer sheath is bonded to a rear section of the radiator and portion of the reflector defining a coaxial tuning cavity of the antenna. A flexible elongated water tube is coaxially inserted in the outer sheath forming an inlet channel in the water tube and outlet channel in the space between the water tube and the outer sheath. The cooling water circulates in the probe cavity cooling down the feed cable and the reflector.

13 Claims, 2 Drawing Sheets

WATER-COOLED FLEXIBLE MICROWAVE ABLATION PROBE

TECHNICAL FIELD

The invention relates to microwave ablation probe and more particularly to a water-cooled flexible microwave ablation probe.

BACKGROUND

Unless otherwise indicated herein, the materials described in this section are not prior art to the claims in this application and are not admitted being prior art by inclusion in this section.

Microwave ablation (MWA) is a form of thermal ablation that uses electromagnetic waves in the microwave energy spectrum to locally heat the tissue and cause tissue necrosis. It is a minimally invasive technique for direct application of an energy-based thermal therapies to a target tissue to destroy and eradicate it and obtain cellular necrosis. Microwave ablation probes are usually used in the treatment of solid tumors as well as the treatment of varicose veins, reticular or spider veins. Because of its high efficiency to control small tissue destruction zones, it has been widely recognized as an alternative to surgery, such as Oncology surgery.

The advantages of MWA ablation compared to surgical treatment are faster recovery, reduced morbidity and mortality, lower procedural cost, accurate targeting under ultrasound or CT scan image guidance, and daycare treatments, thus reducing the hospital stay, and is easily repeatable if residual lesion is present. The microwave ablation probe has greatly improved the power tolerance and the true spherical performance of the ablation area. It's use also expanded from the ultrasound guided environment to the magnetic resonance (MR) guided environment and has become the main ablative probe type on the market. More and more countries have adopted this safe, effective, and less invasive method especially for cancer treatment.

In general, microwave ablation probes known in the prior art are rigid and straight probes with a metallic shaft, which are inserted into the target tissue along a straight path for ablation by percutaneous puncture under the guidance of ultrasound or Computed tomography (CT), or disclose flexible ablation probes that are only suitable for low-power applications, such as coagulation closure of varicose veins, and are not suitable for ablation of larger solid tumors. For example, Chinese patent CN103006321, discloses a water-cooled ablation microwave probe that has acrylonitrile butadiene styrene (ABS) protection handle and an antenna rod body with an outer thin-wall casing pipe which is making such ablation probes rigid and straight. The international patent application WO2016074344 discloses non-magnetic water-cooled microwave ablation probe with an electrode core that is inserted into an inner hole of a puncture head. The puncture head is made from hard crystals, such as zirconia. A ceramic adhesive can also be applied to the outer surface of the electrode core and inner hole of punctured head. The international patent application WO2018/192325 discloses round microwave ablation antenna which uses a chamber for accommodating the coaxial cable and a water diversion pipe. All the these known prior art ablation probes are rigid and straight probes, using metallic shaft, that are inserted into the target tissue along a straight path for ablation by percutaneous puncture under the guidance of ultrasound or Computed tomography (CT).

Another known microwave ablation probe, disclosed in U.S. Pat. No. 11,786,303 uses a semirigid (partially flexible) coaxial cable so that the antenna can be inserted into the tubular channels of the patients. However, such probe is only suitable for low-power applications as no water-cooling is provided, and therefore is not suitable for ablation of larger solid tumors.

Today, as surgical robots become increasingly mature, the microwave ablation antenna needs to be deployed to the target through the narrow working channel of the robot, which has requirements on size of the diameter of the microwave ablation antenna and the length of the microwave ablation probe. To limit the size of the microwave probe and maintain the overall flexibility of the probe, the flexible microwave probe must use a large amount of plastic material and glue. Temperature resistance of plastic materials and glue is generally lower than that of metal materials, and these materials cannot withstand the heat generated by the high microwave power.

With the expansion of the application of microwave ablation technology, more operations need a fully flexible ablation antenna to pass through the human body lumens to the position where straight puncture is difficult to reach for the ablation treatment of large solid tumors, and for the radiated energy of the ablation antenna to reach the strength of a metallic straight probe.

Therefore, there is a need for flexible water-cooled microwave ablation probe that will be easily deployable in the curved human body lumen or can smoothly pass through an endoscope channel or a central channel inside a sliding rod of a surgical robot to reaching out a targeted tissue and destroy and eradicate it, causing cellular necrosis.

SUMMARY OF THE INVENTION

In one aspect a water-cooled flexible microwave ablation probe is provided. The probe comprises a feed coaxial cable with an inner conductor, an outer conductor and a dielectric material therein between the inner conductor and the outer conductor. An outer jacket envelops the outer conductor of the feed cable. An antenna comprises a radiator with a radiating head formed at the front end and a reflector with tubular body. The radiator of the antenna is connected to the inner conductor of the feed cable while the reflector is connected to the outer conductor of the feed cable and a dielectric material is positioned between the radiator and the reflector. An outer sheath that has a flexible tubular body encases the feed cable defining an inner cavity of the probe. The outer sheath has a front end connected to the antenna and an opposite back end that is blocked. A front section of the radiator with the radiating head extends out of the outer sheath. The outer sheath is bonded to an outer surface of a rear section of the radiator and an outer surface of a portion of the reflector defining a coaxial tuning cavity of the antenna. The dielectric material fills the coaxial tuning cavity of the antenna. The probe further comprises a coaxial water-cooling system that is configured to circulate a cooling water in the inner cavity of the probe to cool the feed cable extending therein and the reflector of the antenna. The coaxial water-cooling system comprises a flexible elongated water tube with an outer wall defining water tube's inner cavity. The flexible water tube has a back end that is blocked and an open front end. The flexible water tube is inserted into the inner cavity of the probe such that the flexible water tube is coaxial with the outer sheath and the feed cable in the probe' inner cavity. An inlet channel is formed in the water tube's inner cavity and an outlet channel is formed in a space between the outer sheath and the water tube. A back section of the water tube extends out off the back end of the outer sheath, such that the back end of the outer sheath is tightly sealed. An inlet nozzle that is in communication with a water source is used to inject cooling water into the inlet channel through an opening formed in the rear section of the water tube, and an outlet nozzle that is in communication with the outlet channel is used to circulate water out of the probe through an opening formed in a back section of the outer sheath, such that the cooling water flows in the inlet channel towards the front end of the water tube, flows out of the front end of the water tube making a 180-degree turn in proximity to the rear end of the antenna cooling the reflector and flows back through the outlet channel and out of the outer sheath through the outlet nozzle.

In one aspect, the outer sheath is made from a plastic material, rubber material or other flexible material forming a monolithic outer packaging.

In another aspect, the water-cooled flexible microwave ablation probe is used for treatment of solid tumors.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

DETAILED DESCRIPTION OF SPECIFIC EMBODIMENTS

Figure 1:
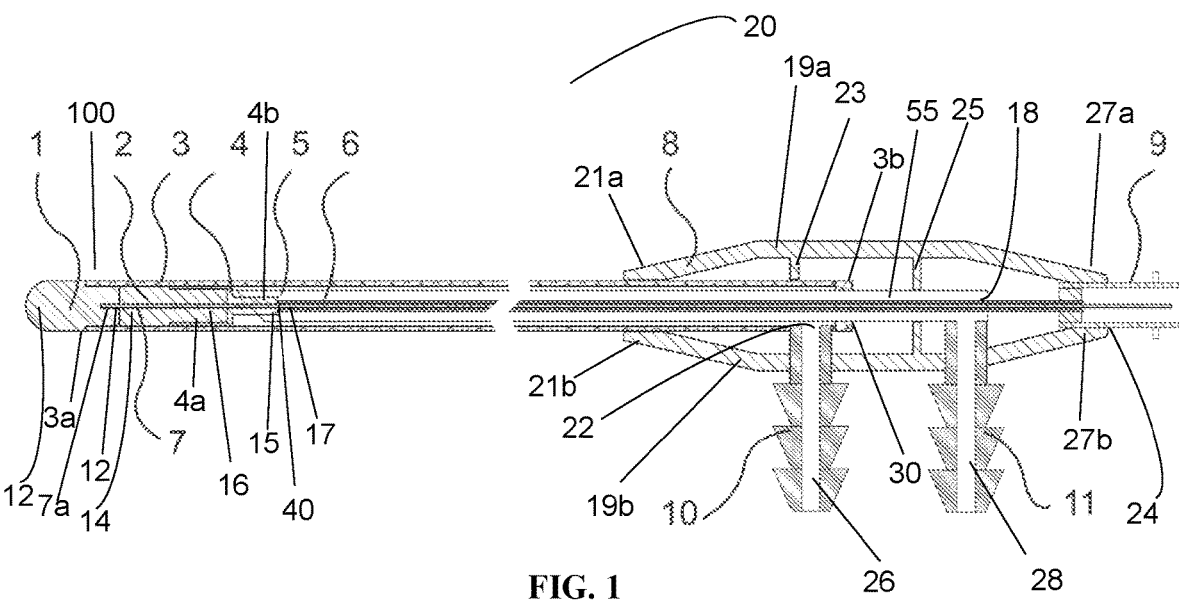
FIG. 1 is a cross sectional view of an example of a water-cooled flexible microwave ablation probe of the present invention.

In order to make the purpose, technical solution and advantages of the present invention clearer, the technical solution in the embodiments of the present invention will be described more clearly and completely in the following with reference to the accompanying drawings.

The present invention relates generally to a water-cooling microwave ablation probe and more particularly, to a water-cooling microwave ablation probe and methods of using water-cooling microwave ablation probe for treatment of solid tumors, such as cancerous tumors. Some microwave ablation applications, require a flexible applicator to reach certain targets through a curved path, so the diameter of the probe can be with a size and a length to fit different ablation applications in the body tissue.

During the microwave ablation, the targeted tissue regions are heated to ablative temperatures while the non-targeted tissue regions are not affected or damaged. In general, the microwave ablation probes comprise a feeding cable terminated by a radiating antenna so that an electric field radiated by the antenna is absorbed in surrounding tissue leading to heating of such tissue. Typically, current travels toward the antenna on the inner conductor surface and inside surface of the outer conductor. A part of the current can travel back toward the microwave generator on the outer surface of the outer conductor due to impedance mismatch between the antenna and the feed coaxial cable and the unbalanced structure of the cable. Such reflected current can generate unwanted heat along the feed coaxial cable and decreases the efficiency of the ablation probe.

Because the feeding cable is made of conductors and dielectric materials, it can heat up when the microwave electromagnetic energy supplied from the microwave generator passes through there. In order to limit the size of the microwave probe and maintain the overall flexibility of the probe, a large amount of plastic material and adhesive/glue may be used in the flexible microwave probe. Temperature resistance of the plastic and adhesive materials is generally lower than the metal materials, and cannot withstand the heat generated by the high microwave power.

Flexible ablation probes require more plastic materials, and the length of the flexible probe is much larger than that of a rigid metallic probe, often reaching more than 1 meter. For example, the rigid metal probes use percutaneous puncture to reach tumors in the liver, lungs or other organs in the abdominal cavity with a probe length of less than 20 cm. The flexible probes reach the target through the respiratory tract or venous channel, and the length of the flexible probe needs to be more than 100 cm. In general, the power tolerance of the flexible ablation probe is lower than that of a rigid metal straight probe. In order to improve the power tolerance of the flexible probe, the present invention adopts the coaxial water-cooling technology. Cooling water is used to cool and protect the feeding cable and antenna.

The present invention discloses a flexible water-cooled microwave ablation probe with a high mechanical strength, small size and applicable in high-power microwave energy applications while avoiding damage or burn out of a healthy not targeted body tissue. The ablation probe of the present invention can pass through a curved human body lumens, and can also smoothly pass through an endoscope channel or a central channel inside a sliding rod of a surgical robot. With the coaxial water-cooling technology, the ablation probe of the present invention can tolerate high-power microwave energy.

Referring now to FIG. 1, an example of a probe 20 for water-cooled flexible microwave ablation per the present invention is illustrated. The probe 20 has an antenna 100 with a metal radiator 1 formed at a front-end of the probe 20 and a reflector 4. The geometry of the antenna 100 determines the probe's efficiency at transferring power from a feeding cable 6 to the radiating antenna 100. The antenna 100 of the flexible ablation probe 20 is a rigid metal conductor, and the length of the antenna 100 directly affects the bending radius of the channel through which the flexible ablation probe 20 can pass. The smaller the length of the antenna 100, the smaller the bend radius of the channel. The antenna 100 is inserted into an outer sheath 3 such that a portion of the metal radiator 1 of the antenna 100 extends out of the outer sheath 3. The metal radiator 1 has a radiating head 1a, such as for example a hemispherical face 1a. The outer sheath 3 is coupled at a rear end of the radiator 1.

The antenna 100 can be a monopole of dipole antenna and is configured to allow generated electromagnetic energy to be radiated through the hemispherical face/head 1a of the radiator 1. The antenna's design with hemispherical face 1*a* allows to achieve a more hemispherical ablation pattern. In one embodiment, the hemispherical face can be made of any suitable metal. For example, it can be made of a non-magnetic metals or alloys, such as for example, a titanium, an aluminum, bronze, or gold- or silver-plated materials to allow real time visualization under Magnetic Resonance Imaging (MM). In one implementation, the face or head of the radiator 1 can be sharpened at the tip.

The outer sheath 3 can have generally cylindrical tubular elongated body with an inner cavity with a prearranged diameter and length. The outer sheath 3 can have an oblique front end 3*a* connected to the rear end of the radiator 1 and an opposite back end 3*b*. The back end 3*b* of the outer sheath 3 is tightly sealed. The radiator 1 may have a front section, such as the metal radiating head 1*a*, a rear section 1*b* that can be a metal cylinder of various lengths ranging in millimeters. The metal radiating head 1*a* extends out of the outer sheath 3 and is intended to directly contact a target tissue to improve the ablation efficiency. At least portion of the rear section 1*b* extends into and is enveloped and bonded together with the outer sheath 3 using a high-temperature epoxy resin.

The outer sheath 3 can have a fully flexible elongated body, made from a plastic, rubber or other flexible material forming an immersive, monolithic outer packaging. In one embodiment, the outer sheath 3 is made from a flexible plastic. The immersive, monolithic outer packaging provided by the outer sheath 3 provides integration of the flexible probe 20 and improves the mechanical strength and the smoothness of the outer surface of the probe 20. The outer sheath 3 is generally cylindrical, with coaxial cavity that defines an inner cavity 14 with the prearranged diameter and length. The cylindrical outer sheath 3 has an oblique front end and opposite back end, and is made of a flexible plastic material.

The probe 20 further comprises a feed coaxial cable 6 coupled to the antenna 100. The feed coaxial cable 6 has an inner conductor 7 and an outer conductor 17 with a dielectric material between the inner conductor 7 and the outer conductor 17 as an insulator, and an outer jacket enveloping the outer conductor 17 of the coaxial feed cable 6. A second end of the coaxial feed cable 6 is connect to a power source, such as a microwave generator, through a connector 9. The outer conductor 17 of the flexible feed cable 6 can be a metallic braided outer conductor 17 that is coupled to the reflector 4 at its rear end 15. The cable core inner conductor 7, can be a multi-strand metallic wire. The feed cable 6 is extending axially throughout the inner cavity 14 of the outer sheath 3 and is secured in proximity to the radiator 1 at its first end and with microwave generator through a connector 9 at its second end. The flexible feed cable 6 can have different lengths between for example 50 cm to 150 cm.

The reflector 4 of the antenna 100 can have elongated cylindrical body having a first part 4*a* with a diameter to fit tight within the inner cavity 14 of the outer sheath 3 and is coupled to the outer sheath 3 in proximity to the radiator 1, and a second part 4*b* that has a diameter smaller than the diameter of the first part 4*a* of the reflector. The reflector body defines a coaxial resonant/tuning cavity 16 of the antenna 100. The geometry of the coaxial tuning cavity 16 is important since it determines the output frequency of the generated energy. The reflector 4 can be centrally positioned in the turning cavity 16. The dielectric material 2 fills the coaxial cavity 16 providing mechanical strength to the antenna 100 and acts as a waveguide for the electromagnetic energy in the radiator 1 as well as an insulator between the reflector 4 and the outer sheath 3. Having a reflector 4 with a diameter greater than the diameter of the core (inner conductor 7) of the feed coaxial cable 6 prevents the burn out due to the overheating of the core 7 of the feed coaxial cable 6. In one embodiment, the first part 4*a* of the reflector 4 can have number of steps, wherein each step can have increased diameter with the step section that is closer to the radiator having the larger diameter. The number of steps in the first part 4*a* of the reflector 4 depends on the diameter of the antenna 100. For example, more steps can be used for probe 20 with larger diameters while less steps can be used in probe with smaller diameter. In addition, the geometry of the reflector 4 with dielectric material 2 define the geometry of the tuning cavity 16, such that matching performance of a microwave circuit can be improved by adjusting the depth and the diameter of the tuning cavity 16. The tuning matching cavity 16 of the antenna 100 can compensate the mismatch of the microwave circuit caused by reducing the length of the antenna and improve the radiation efficiency of the antenna. In general, to efficiently delivery microwave energy, the length of a microwave antenna is fixed, and the length of a single antenna pole must be up to a quarter wavelength. For example, multiple steps in the reflector 4 can form multiple, serially connected, quarter-wave dielectric portions that can be used to vary the impedance of the antenna 100 to obtain a good match of the impedances between the antenna 100 and the feed coaxial cable 6, so that a shorter antenna can be used without sacrificing the efficiency of the probe 20. The insulator 2 can be a microwave insulating material, such as polytetrafluoroethylene (PTFE), polyamide, epoxy resin, or any other suitable dielectric material, and can be machined or casted to the shape of the space between the radiator 1 and the reflector 4, and the outer sheath 3.

The inner conductor 7 of the feed cable 6 passes through a central through-hole 40 formed in the reflector 4. The inner conductor 7 is a flexible metallic multi-strand wire, and the inner conductor 7 and the insulator 2 penetrate through the antenna reflector 4 and the tuning cavity 16. A first end 7*a* of the inner conductor 7 extends forward to penetrate through a mounting hole 12 in the center of the radiator 1 and is welded or riveted to the radiator to form good electrical connectivity. The second part 4*b* of the reflector 4 is welded to the outer conductor 17, i.e., a metallic braided outer layer 17, to form electrical connectivity, while the multi-strand metallic inner conductor 7 penetrates out of the feeding cable 6 and through the opening 40 formed in the reflector 4, enters the mounting hole 12 positioned in the center of the radiator 1. The distance between the radiator 1 and the reflector 4 can be about 2 mm.

The portion 1*b* of the antenna radiator 1 and the part 4*a* of the metal antenna reflector 4 are enclosed and bonded to the outer sheath 3 of the ablation probe 20 using a high-temperature glue. The outer sheath 3 extends from its front end 3*a* that is coupled to the antenna 100 to its back end 3*b* that is coupled to a handle 8. The handle 8 has an upper part 19*a* and a lower part 19*b*. The rear portion/section of the outer sheath 3 extend into an inner space between the upper and lower parts 19*a* and 19*b* of the handle 8. A first end 21*a*, 21*b* of each of the upper and lower parts 19*a* and 19*b* of the handle 8 are connected to the outer surface of the outer sheath 3 of the probe 20. A second end 27*a*, 27*b* of each of the upper and lower parts 19*a* and 19*b* of the handle 8 are connected to the connector 9. The handle 8 has an opening 24 formed at the second end 27*a*, 27*b* of the upper and lower parts 19*a* and 19*b* sized to receive and secure to an end portion of the connector 9. The handle 8 can further comprise one or more support elements 23, 25 that extend from the upper part 19*a* and/or the lower part 19*b* to secure the probe housing (e.g., sheath 3) to the handle 8.

The water-cooled flexible microwave ablation probe 20 further comprises a coaxial water-cooling system 50 having a flexible water tube 5 that extends in the inner cavity 14 of the outer sheath 3. The flexible water tube 5 can be made of a flexible plastic material. The coaxial water-cooling system further comprises a cooling-water outlet nozzle 10 coupled to and in communication with an outlet channel 5*b* and a cooling-water inlet nozzle 11 that is coupled to and in communication with an inlet channel 5*a* (see FIG. 2). The cooling-water outlet nozzle 10 communicate with the outlet channel 5*b* through an opening 22 formed in the sheath 3. The cooling-water inlet nozzle 11 communicate with the inlet channel 5*a* through an opening 32 formed in a wall of the flexible tube 5.

Figure 2:
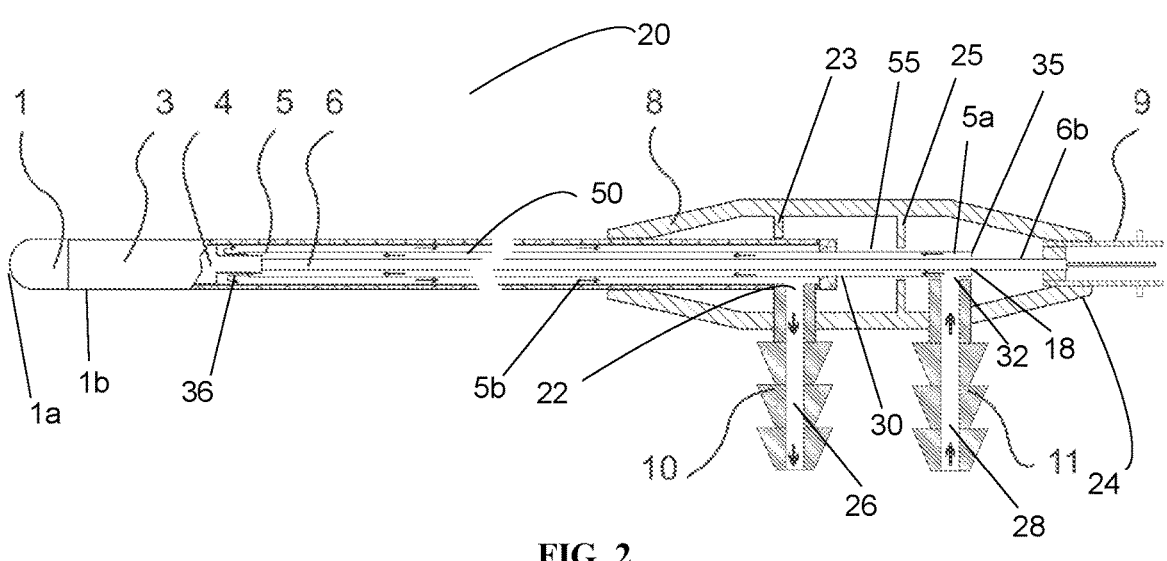
FIG. 2 is a partial cross-sectional view of the water-cooled flexible microwave ablation probe of FIG. 1 showing coaxial water channels in the water-cooled flexible microwave ablation probe.

FIG. 2 illustrates the probe 20 and the coaxial water-cooling system 50. The flexible tube 5 of the coaxial water-cooling system has a back end 35 that is blocked to prevent water leak and an open front end 36. The flexible tube 5 is connected and in communication with the inlet nozzle 11 through the opening 32 formed in the wall of the tube 5 in proximity to its back end 35. A cooling-water is injected into the tube 5 through the inlet water nozzle 11 and the opening 32. The water tube 5 is inserted in the inner cavity 14 of the outer sheath 3, such that the front open end 36 of the water tube 5 is positioned in proximity to the reflector 4, such that the water tube 5 envelops the second part 4*b* of the reflector 4 and the feed cable 6. A back part 55 of the flexible water tube 5 extends out of the outer sheath 3 through an opening 30 formed in the back end 3*b* of the outer sheath 3. The back end 3*b* is sealed (e.g., by using a water plugging ring) to prevent any water leak through the opening 30. A rear portion 6*b* of the feed cable 6 extends out of the water tube 5 through an opening 18 formed in the back end 35 of the water tube 5. The opening 18 at the back end 35 is sealed so that no cooling water leaks through the opening 18. For example, a water plugging ring can be provided around the opening 18 to prevent water leaks. The water tube 5 is coaxial with the feed cable 6 (that is encased in the outer jacket) and the outer sheath 3 such that the inlet channel 5*a* is formed inside the flexible tube 5 while the outlet channel 5*b* is formed in the space between the outer surface of the tube 5 and the inner surface of the outer sheath 3. The cooling water in injected into the flexible tube 5 through the inlet nozzle 11. The water flows in the inlet channel 5*a* cooling the portion of the feed cable 6 that is in the flexible water tube 5 towards the front end 36, flows out (spills over) the front end 36 making 180 degrees, turns back in proximity to a rear part 4*b* of the reflector 4 thereby cooling the reflector 4, and flows back through the outlet channel 5*b* and out of the outer sheath 3 through the outlet nozzle 10. As the cooling water inlet channel 5*a*, the cooling water outlet channel 5*b* and the feed cable 6 are coaxially arranged, the water in both inlet channel 5*a* and outlet channel 5*b* can cool the feed cable 6, thereby preventing the human body lumens through which the probe passes from being damaged due to high temperature of the probe shaft. The inlet nozzle 11 and the outlet nozzle 10 are connected to a water pump to provide water circulation. For example, the water pump can be an external peristaltic pump, however any other suitable water pump can be used. The cooling water makes a 180-degree turn at the front end 36 of the flexible tube in proximity of the antenna reflector 4 and enters the outer channel 5*b* to return to the outlet nozzle 10. The cooling water circulates to continuously cool the antenna 100 and the probe body, thus keeping the microwave antenna and the probe body at a low temperature during operation to reduce the carbonization of tissues around the antenna, protecting the probe passage channels (i.e., a channel in the sliding rod of the surgical robot or an endoscope channel) from being damaged by heat and preventing possible water leakage caused by the loss of mechanical strength and flexibility by denaturation of non-metallic materials such as plastics and glue at high temperatures, improving the power tolerance of the ablation probe.

Figure 3:
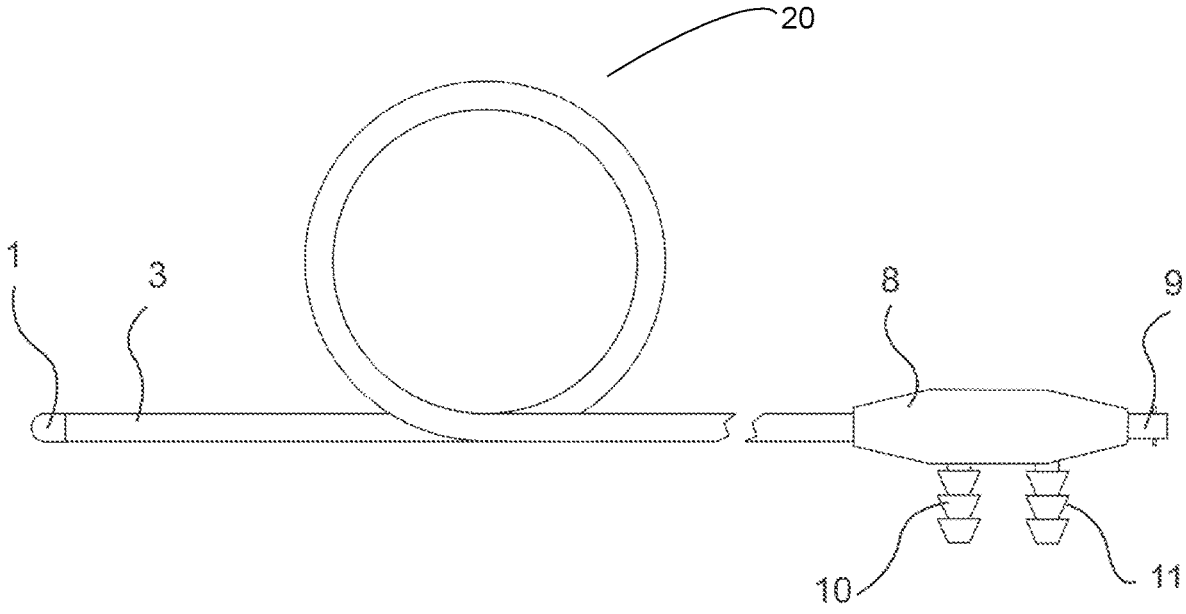
FIG. 3 is a side view of an example of a water-cooled flexible microwave ablation probe of the present invention.

In one embodiment, the coaxial water-cooling system, can comprise a larger water outer tube that is sleeved outside a smaller water inner tube. The outer sheath 3 is directly sleeved over the outer water tube. The flexible coaxial cable 6 encased in the outer jacket is placed inside the inner water tube, and a space between the coaxial cable and the inner surface of the water inner tube forms the water inlet channel. Cooling-water enters the water inlet channel from the water inlet nozzle 11 (that is in communication with the smaller inner tube), flows in the inner tube along and in proximity to feed cable and the antenna reflector 4, and flows out from the opening at an end of inner water tube and enters the water outlet channel formed in the space between the outer tube and the inner tube, and then flows out from the water outlet nozzle 10. Referring now to FIG. 3, an example of a probe 20 for water-cooling flexible microwave ablation per the present invention is illustrated. The probe 20 includes the radiating antenna 100 having the radiating head at the front end and the plastic flexible probe outer sheath 3. The flexible outer sheath 3 has an inner cavity with predetermined diameter that can fit antenna's reflector and the coaxial water-cooling flexible tube 5. The flexible feed cable 6 enters axially through the water tube 5 into the probe. The probe further comprises a handle 8 that connects the probe 20 to the microwave coaxial connector 9. The microwave generator is used as a power source, such as for example a magnetron, and can provide microwave electromagnetic energy of a frequency of 2.45±0.05 GHz range. The flexible probe outer sheath 3 can be fully flexible so that the antenna 100 can be inserted into the tubular channels of the patients, such as solid tumours.

While particular elements, embodiments and applications of the present disclosure have been shown and described, it will be understood, that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another or may be combined in various ways.

All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The example calculations, simulations, results, graphs, values, and parameters of the embodiments described herein are intended to illustrate and not to limit the disclosed embodiments. Other embodiments can be configured and/or operated differently than the illustrative examples described herein.

The invention claimed is:

1. A water-cooled flexible microwave ablation probe comprising:

a feed coaxial cable having an inner conductor, an outer conductor, a dielectric material positioned therein between the inner conductor and the outer conductor, and an outer jacket that envelops the outer conductor;

an antenna comprising:

a radiator having a solid body with a radiating head formed at a distal end of the radiator, the radiator coupled to the inner conductor of the feed cable;

a reflector coupled to the outer conductor of the feed cable and having an elongated cylindrical body with a diameter greater than a diameter of the feed cable, the reflector having a central opening formed in its proximal end such that a first end of the inner conductor of the feed coaxial cable passes through the reflector's opening and is secured into a proximal section of the radiator; and dielectric material positioned between the radiator and the reflector;

an outer sheath having a flexible tubular elongated body defining an inner cavity of the water cooled flexible microwave ablation probe with a predetermined diameter and length, the outer sheath having a distal end connected to the antenna and a blocked proximal end, a distal section and the radiating head of the radiator extends out of the outer sheath, the outer sheath is bonded to an outer surface of the proximal section of the radiator and an outer surface of a portion of the reflector defining a coaxial tuning cavity of the antenna, the dielectric material positioned between the radiator and the reflector is filling the coaxial tuning cavity of the antenna;

a coaxial water-cooling system configured to circulate a cooling water in the inner cavity of the water-cooled flexible microwave ablation probe to cool the feed coaxial cable extending therein and the reflector of the antenna, the coaxial water-cooling system comprises:

a flexible elongated water tube having a blocked proximal end and an open distal end is inserted into the inner cavity of the water-cooled flexible microwave ablation probe such that the flexible elongated water tube is coaxial with the outer sheath and the feed coaxial cable, an inlet channel is formed inside the flexible elongated water tube and an outlet channel is formed in a space between the outer sheath and the flexible elongated water tube, a proximal section of the flexible elongated water tube extending out of the proximal back end of the outer sheath, an inlet opening is formed in a wall of the flexible elongated water tube in proximity to its blocked proximal end and an outlet opening is formed in a wall of the outer sheath in proximity to the blocked proximal end, an inlet nozzle is in communication with the inlet opening is configured to inject the cooling water into the inlet channel, an outlet nozzle is in communication with the outlet opening; and a microwave generator connected to the water-cooled flexible microwave ablation probe to generate an electromagnetic energy that is transmitted to the antenna by the feed coaxial cable, wherein the cooling water is configured to be injected into the flexible elongated water tube through the inlet opening, is configured to flow in the inlet channel towards the distal end of the water tube, is configured to flow out of the distal end of the flexible elongated water tube making a 180-degree turn in proximity to the proximal end of the reflector and is configured to flow back through the outlet channel and out of the outer sheath through the outlet nozzle therefore cooling the feed coaxial cable positioned in the flexible elongated water tube and the reflector.

2. The water-cooled flexible microwave ablation probe of claim 1, wherein the radiating head of the antenna has a hemispherical shape, the generated electromagnetic energy is configured to be radiated out through the radiating head.

3. The water-cooled flexible microwave ablation probe of claim 1, wherein the reflector comprises a first part and a second part, a diameter of the first part of the reflector being greater than a diameter of the second part of the reflector.

4. The water-cooled flexible microwave ablation probe of claim 3, wherein the first part of the reflector includes a number of steps, wherein each step that is further away from the second part has an increased diameter such that a step section of the first part that is closer to the proximal section of the radiator has a largest diameter, the number of steps in the first part of the reflector depends on a diameter of the antenna.

5. The water-cooled flexible microwave ablation probe of claim 3, wherein a geometry of the reflector with the dielectric material positioned between the radiator and the reflector defines a geometry of the coaxial tuning cavity of the antenna.

6. The water-cooled flexible microwave ablation probe of claim 1, wherein the radiator of the antenna has a mounting cavity formed centrally in the proximal section of the radiator, the first end of the inner conductor is configured to penetrates into the mounting cavity to form good electrical connectivity.

7. The water-cooled flexible microwave ablation probe of claim 6, wherein the first end of the inner conductor is welded or riveted into the mounting cavity of the radiator.

8. The water-cooled flexible microwave ablation probe of claim 1, wherein the inner conductor is a multi-strand metallic wire and the outer conductor is a metallic braided wire.

9. The water-cooled flexible microwave ablation probe of claim 1, wherein the distal end of the outer sheath is bonded to the proximal section of the radiator with a high-temperature epoxy resin.

10. The water-cooled flexible microwave ablation probe of claim 1, wherein the outer sheath is made from a plastic material or rubber material.

11. The water-cooled flexible microwave ablation probe of claim 1, wherein the flexible elongated water tube comprises a central opening formed in its proximal back end, the feed cable passes through the central opening, the proximal back end of the flexible elongated water tube is sealed to prevent water leak.

12. The water-cooled flexible microwave ablation probe of claim 1, wherein operating frequency of the microwave generator is 2.45±0.05 GHz.

13. The water-cooled flexible microwave ablation probe of claim 1, wherein the dielectric material between the radiator and the reflector is selected form a polytetrafluoroethylene (PTFE), a polyamide, or an epoxy resin.

* * * * *